US005977165A

United States Patent [19]

Agatsuma et al.

[11] Patent Number: 5,977,165

[45] Date of Patent: Nov. 2, 1999

[54] RADICICOL DERIVATIVES

[75] Inventors: Tsutomu Agatsuma; Yutaka Saitoh; Yoshinori Yamashita; Tamio Mizukami, all of Tokyo; Shiro Akinaga, Shizuoka; Katsushige Gomi, Shizuoka; Kazuhito Akasaka, Shizuoka; Isami Takahashi, Tokyo, all of Japan

[73] Assignee: Kyowa Hakko Kogyo Co., Ltd., Tokyo, Japan

[21] Appl. No.: 08/958,285

[22] Filed: Oct. 27, 1997

Related U.S. Application Data

[63] Continuation of application No. PCT/JP96/01158, Apr. 26, 1996.

[30] Foreign Application Priority Data

Apr. 26, 1995 [JP] Japan .................................... 7-102626

[51] Int. Cl.$^6$ ........................ A61K 31/335; C07D 313/00

[52] U.S. Cl. ........................... 514/450; 549/268; 549/270

[58] Field of Search ..................................... 549/268, 270; 514/450

[56] References Cited

U.S. PATENT DOCUMENTS

| | | | |
|---|---|---|---|
| 4,228,079 | 10/1980 | Calton | 260/343.41 |
| 5,597,846 | 1/1997 | Sugimura et al. | 514/450 |

FOREIGN PATENT DOCUMENTS

| | | |
|---|---|---|
| 460950 | 12/1991 | European Pat. Off. . |
| 606044 | 7/1994 | European Pat. Off. . |

OTHER PUBLICATIONS

Mol. Gen. Genet., 236 (2–3) (1993) pp. 347–354.
Cancer Research, 52 (24) (Dec. 1992 6926–6930.
Chemical Abstracts, vol. 127: 176300 (Abst. of Shibata et al, Jpn. Kokai Tokyo Koho JP 09202781 Aug. 5, 1997).
P. Chanmugan, et al., Journal of Biological Chemistry, vol. 270, No. 10, Mar. 10, 1995, pp. 5418–5426.

*Primary Examiner*—Bernard Dentz
*Attorney, Agent, or Firm*—Fitzpatrick, Cella, Harper & Scinto

[57] ABSTRACT

The present invention relates to radicicol derivatives represented by the following formula (I) or pharmacologically acceptable salts thereof:

(I)

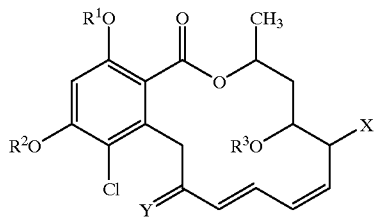

wherein $R^1$ and $R^2$ are the same or different and each represents hydrogen, alkanoyl, alkenoyl or tert-butyldimethylsilyl; (1) when X represents halogen, Y represents an oxygen atom or $R^4$—O—N (wherein $R^4$ represents hydrogen or substituted or unsubstituted lower alkyl); and $R^3$ represents hydrogen, alkanoyl, alkenoyl or the like; and (2) when X and $R^3$ are combined with each other to represent a single bond; Y represents $R^{4B}$—O—N (wherein $R^{4B}$ has the same meaning as $R^4$). The radicicol derivatives of the present invention demonstrate tyrosine kinase inhibition activity and pharmacological activities such as antitumor, antimicrobial or immunosuppression effects.

4 Claims, No Drawings

RADICICOL DERIVATIVES

This application is a continuation of pending application No. PCT/JP96/01158, filed on Apr. 26, 1996.

TECHNICAL FIELD

The present invention relates to novel radicicol derivatives or pharmacologically acceptable salts thereof which show tyrosine kinase inhibition activity and have antitumor, antimicrobial or immunosuppression effects.

BACKGROUND ART

It is known that microbial metabolite radicicol represented by the following formula (B) has an antifungal effect and an anticancer effect [*Nature,* 171, 344 (1953); *Neoplasma,* 24, 21 (1977)] or an immunosuppression effect (Japanese Published Unexamined Patent Application No. 298764/94).

(B)

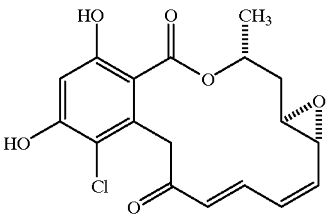

Furthermore, it is known that radicicol derivatives in which the phenolic hydroxyl group is modified with various acyl groups have an antitumor effect (Japanese Published Unexamined Patent Application No. 226991/92). In addition, it is disclosed that radicicol derivatives in which the phenolic hydroxyl group is modified with an acyl group or an alkyl group show an angiogenesis inhibition effect (Japanese Published Unexamined Patent Application No. 279279/94).

Tyrosine kinase is an enzyme which uses ATP as a phosphate donor and catalyzes transfer of its γ-phosphate group to the hydroxyl group of a specified tyrosine residue of a substrate protein, thereby taking an important role in the control mechanism of intracellular signal transduction. Various tyrosine kinase families are known, and it is known that tyrosine kinase activities (e.g., Src in colon cancer, ErbB-2 in breast cancer and gastric cancer, Abb in leukemia, and the like) increase. Disordered increase in the tyrosine kinase activity causes abnormal differentiation and proliferation of cells. In consequence, specific inhibitors of tyrosine kinase are useful in preventing and treating various diseases, including as antitumor agents.

Lck is a tyrosine kinase which is activated when T lymphocytes are activated by antigen stimulation, and an inhibitor of this enzyme is useful as an immunosuppressant. Also, it is known that Src is concerned in bone resorption in osteoclast, and an inhibitor of this tyrosine kinase is useful as a bone resorption inhibitor for the treatment of osteoporosis. In addition, inhibitors of EGF-R (epidermal growth factor receptor), FGF-R (fibroblast growth factor receptor), PDGF-R (platelet-derived growth factor receptor) and the like as receptor type tyrosine kinases of various growth factors are useful as a solid cancer growth inhibitor, an angiogenesis inhibitor, a vascular smooth muscle growth inhibitor and the like.

The inhibitory effect of the tyrosine kinase activity can be measured by carrying out Western blotting analysis with an anti-phosphotyrosine antibody using a rat fibroblast cell strain SR-3Y1 transformed with an oncogene v-Src (available from RIKEN Gene Bank) and calculating the amount of intracellular protein in which tyrosine is phosphorylated. Since the tyrosine phosphorylation level of intracellular protein in SR-3Y1 cells for use in this method is increased by v-Src tyrosine kinase, the ability of radicicol derivatives to inhibit v-Src tyrosine kinase can be detected as reduction of the amount of protein in which tyrosine is phosphorylated. Robinson, S. P. et al. [*International Journal of Oncology,* 2, 253 (1993)] report a method for examination of tyrosine phosphorylation inhibition effect by Western blotting analysis, and Kwon, H. J. et al. [*Cancer Research,* 52, 6926 (1992)] report examples of experiment using SR-3Y1 cells.

DISCLOSURE OF THE INVENTION

An object of the present invention is to provide novel radicicol derivatives or pharmacologically acceptable salts thereof which show tyrosine kinase inhibition activity and have antitumor, antimicrobial or immunosuppression effects.

The present invention relates to radicicol derivatives represented by the following formula (I) or pharmacologically acceptable salts thereof:

(I)

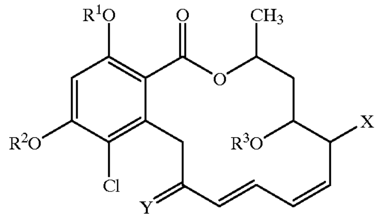

wherein $R^1$ and $R^2$ are the same or different and each represents hydrogen, alkanoyl, alkenoyl or tert-butyldimethylsilyl;

(1) when X represents halogen,

Y represents an oxygen atom or $R^4$—O—N

{wherein $R^4$ represents hydrogen or substituted or unsubstituted lower alkyl (said substituent is selected from hydroxyl, lower alkoxy, lower alkanoyloxy, azido, amino, mono- or di-lower alkylamino, lower alkanoylamino, lower alkoxycarbonylamino, lower alkenyloxycarbonylamino, carboxy, lower alkoxycarbonyl, lower alkylcarbamoyl and cyclic imido}; and $R^3$ represents hydrogen, alkanoyl, alkenoyl or —SO—Z <wherein Z represents the following formula (A):

(A)

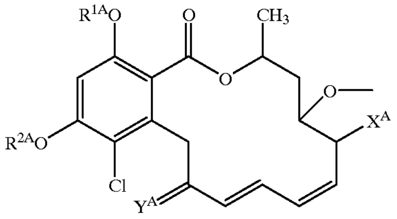

{wherein $X^A$, $R^{1A}$ and $R^{2A}$ have the same meaning as X, $R^1$ and $R^2$, respectively; and $Y^A$ represents an oxygen atom or $R^{4A}$—O—N (wherein $R^4$A has the same meaning as $R^4$)}>; and (2) when X and $R^3$ are combined with each other to represent a single bond;

Y represents $R^{4B}$—O—N (wherein $R^{4B}$ has the same meaning as $R^4$)

Hereinafter, the compound represented by formula (I) will be called Compound (I). Compounds of other formula numbers with also be called in the same manner.

In the definition of each group of Compound (I), the alkanoyl means a straight or branched group having 1 to 20 carbon atoms (e.g., formyl, acetyl, propanoyl, butanoyl, caproyl, lauroyl, myristoyl, palmitoyl, stearoyl and the like). The alkenoyl means a straight or branched group having 3 to 20 carbon atoms (e.g., palmitoleoyl, linoleoyl, linolenoyl and the like). The halogen means an atom of fluorine, chlorine, bromine or iodine. The lower alkyl means a straight or branched group having 1 to 8 carbon atoms (e.g., methyl, ethyl, propyl, isopropyl, butyl, isobutyl, sec-butyl, tert-butyl, pentyl, isopentyl, hexyl, heptyl, octyl and the like).

The substituent of the substituted lower alkyl is the same or different 1 to 3 groups (e.g., hydroxyl, lower alkoxy, lower alkanoyloxy, azido, amino, mono- or di-lower alkylamino, lower alkanoylamino, lower alkoxycarbonylamino, lower alkenyloxycarbonylamino, carboxy, lower alkoxycarbonyl, lower alkylcarbamoyl, cyclic imido and the like). The lower alkylcarbamoyl means a group substituting 1 to 2 lower alkyl on the nitrogen atom of carbamoyl.

Herein, the lower alkyl moiety of the lower alkoxy, lower alkanoyloxy, mono- or di-lower alkylamino, lower alkanoylamino, lower alkoxycarbonylamino, lower alkoxycarbonyl and lower alkylcarbamoyl is the same as the lower alkyl defined above, and one of its carbon atoms may be substituted with a silicon atom. The lower alkenyl moiety of the lower alkenyloxycarbonylamino represents a straight or branched group having 2 to 6 carbon atoms (e.g., vinyl, allyl, butenyl, pentenyl, hexenyl, pentadienyl, hexadienyl and the like). The cyclic imido represents, for example, phthalimido, succinimido, glutarimido and the like.

The pharmacologically acceptable salt of Compound (I) include an acid addition salt, a metal salt, an ammonium salt, an organic amine addition salt, an amino acid addition salt and the like. Examples of the acid addition salt include inorganic acid salts (e.g., hydrochloride, hydrobromide, sulfate, phosphate and the like), and organic acid salts (e.g., formate, acetate, oxalate, benzoate, methanesulfonate, p-toluenesulfonate, maleate, fumarate, tartrate, citrate, succinate, lactate and the like). Examples of the metal salt include alkali metal salts (e.g., lithium salt, sodium salt, potassium salt and the like), alkaline earth metal salts (e.g., magnesium salt, calcium salt and the like), aluminum salt, zinc salt and the like. Examples of the ammonium salt include salts with ammonium, tetramethylammonium and the like. Examples of the organic amine addition salt include addition salts with morpholine, piperidine and the like. Examples of the amino acid addition salt include addition salts with glycine, phenylalanine, aspartic acid, glutamic acid, lysine and the like.

The compound of the present invention is obtained generally using the optically active radicicol as the starting material, and all of possible stereoisomers and their mixtures are included in the present invention.

Next, a production method of Compound (I) is described.

The process for producing Compound (I) comprises reaction steps mainly including oxime formation (step 1), halohydrin formation (step 2) and acylation (step 3). These reaction steps can be combined depending on the object compound.

In the production method shown below, when a defined group changes under the employed method or is not fit for carrying out the method, the object compound can be obtained by using an introduction-elimination method of protecting groups usually used in organic synthetic chemistry [for example, see Protective Groups in Organic Synthesis, T. W. Greene, John Wiley & Sons Inc. (1981)]. Also, if necessary, the order of reaction steps such as introduction of substituents may be changed.

Production Method 1

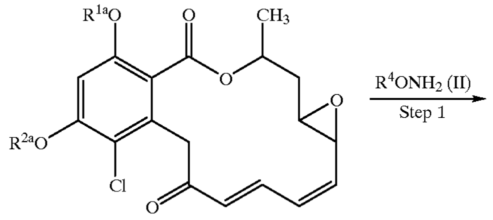

(C)

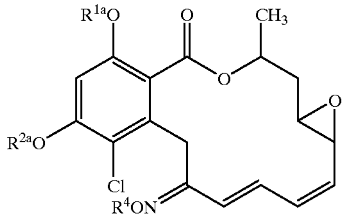

(Ia)

(In the above formula, $R^{1a}$ and $R^{2a}$ are groups in which tert-butyldimethylsilyl is removed from $R^1$ and $R^2$, respectively, defined above; and $R^4$ has the same meaning as defined above.)

Step 1

Radicicol or Compound (C) which is obtained from radicicol by a known method (Japanese Published Unexamined Patent Application No. 226991/92) is used as the starting material compound.

Compound (Ia) can be obtained by allowing Compound (C) to react with Compound (II) or an acid addition salt thereof. Pyridine, chloroform, dichloromethane, ether, tetrahydrofuran, dimethylformamide, acetonitrile and the like may be used as the reaction solvent either alone or as a mixture thereof. When an acid addition salt of Compound (II) is used, the reaction is carried out in the presence of a base, for example, an amine (e.g., pyridine, triethylamine, diisopropylethylamine or the like), or an alkali metal carbonate or bicarbonate (e.g., sodium carbonate, potassium carbonate or the like), in an amount of 1 equivalent or more based on the acid addition salt of Compound (II), preferably using pyridine which also serves as the solvent. Compound (II) or its acid addition salt is used in an amount of generally 1 equivalent or more, preferably 2 to 10 equivalents, based on radicicol. The reaction is carried out generally at 20 to 100° C. for 1 to 80 hours.

Production Method 2

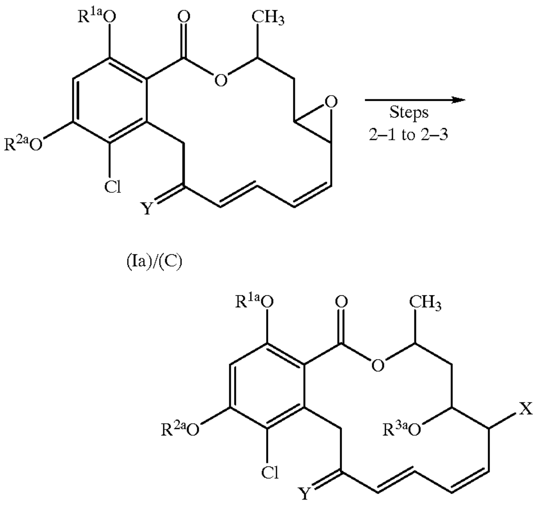

(Ia)/(C)

(Ib)

{In the above formula, $R^{1a}$, $R^{2a}$, X and Y have the same meaning as defined above; and $R^{3a}$ represents hydrogen, formyl or —SO—Z (wherein Z has the same meaning as defined above).}

Step 2-1

A member of Compound (Ib) in which $R^{3a}$ is hydrogen can be obtained by allowing Compound (Ia) or (C) to react with an acid (e.g., hydrogen chloride, hydrogen bromide or the like) or Lewis acid (e.g., titanium tetrachloride or the like). Dioxane, tetrahydrofuran, ether, chloroform, dichloromethane, dimethylformamide, acetonitrile and the like may be used as the solvent either alone or as a mixture thereof. The acid or Lewis acid is used in an amount of 1 equivalent or more, preferably 1 to 10 equivalents, based on Compound (Ia) or (C). The reaction is carried out generally at −20 to 40° C. for 10 minutes to 48 hours.

Step 2-2

A member of Compound (Ib) in which $R^{3a}$ is formyl can be obtained by allowing Compound (Ia) or (C) to react with oxalyl chloride, phosphorous oxychloride or phosphorous oxybromide in dimethylformamide. Phosphorous oxychloride or phosphorous oxybromide is used in an amount of 1 equivalent or more, preferably 2 to 5 equivalents, based on Compound (Ia) or (C). The reaction is carried out generally at −10 to 40° C. for 1 to 48 hours.

Step 2-3

A dimer compound of Compound (Ib) in which $R^{3a}$ is —SO—Z (wherein Z has the same meaning as defined) can be obtained by allowing Compound (Ia) or (C) to react with thionyl chloride or thionyl bromide. Dimethylformamide, chloroform, dichloromethane, dimethyl sulfoxide, acetonitrile and the like may be used as the solvent either alone or as a mixture thereof. Thionyl chloride or thionyl bromide is used in an amount of 1 equivalent or more, preferably 2 to 10 equivalents, based on Compound (Ia) or (C). The reaction is carried out generally at −10 to 40° C. for 1 to 48 hours.

Production Method 3

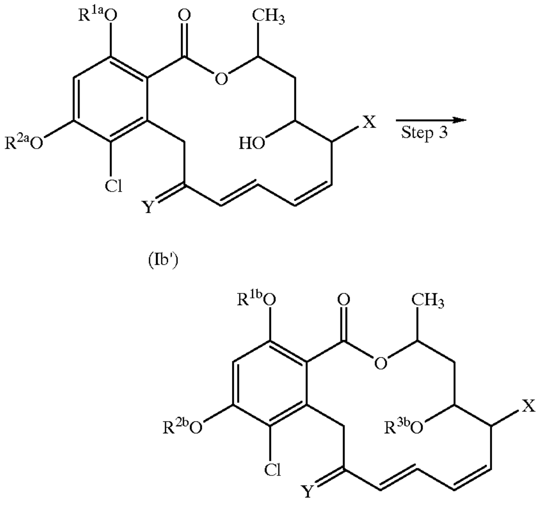

(Ib')

(Ic)

(In the above formula, $R^{1a}$, $R^{2a}$, X and Y have the same meaning as defined above; $R^{1b}$ and $R^{2b}$ have the same meaning as $R^{1a}$ and $R^{2a}$, respectively; and $R^{3b}$ represents alkanoyl or alkenoyl.)

Step 3

Compound (Ic) in which the hydroxyl group is modified with alkanoyl or alkenoyl can be obtained by allowing Compound (Ib') to react with 1 equivalent or more, preferably 1 to 100 equivalents, of an acid halide, an acid anhydride or a mixed acid anhydride having the object alkanoyl or alkenoyl group in the presence of a base. Although modification of optional hydroxyl group can be effected by properly carrying out introduction and elimination of a protecting group of the hydroxyl group, it is possible to modify a plurality of hydroxyl groups at the same time. Pyridine, N,N-dimethylaniline, N,N-diethylaniline or the like is used as the base in an amount of 1 equivalent or more, preferably 1 to 200 equivalents, based on Compound (Ib'). The reaction is carried out in a solvent (e.g., dimethylformamide, dimethyl sulfoxide, chloroform, dichloromethane, toluene or the like). Also, it is possible to use a base (e.g., pyridine or the like) which can also serve as the solvent. In addition, the reaction can be accelerated by adding 0.1 to 4 equivalents of N,N-dimethylaminopyridine or the like. The reaction is carried out generally at −20 to 50° C. for 5 minutes to 24 hours.

Production Method 4

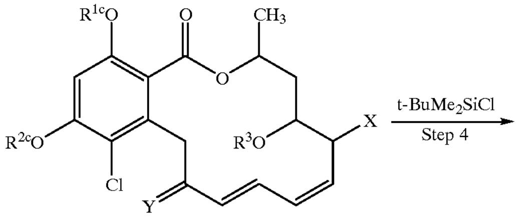

(Id)

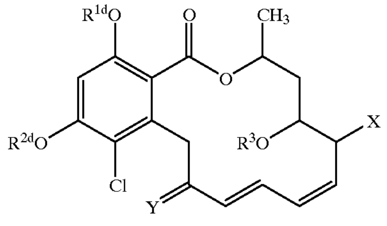

(Ie)

{In the above formula, X, Y and $R^3$ have the same meaning as defined above; $R^{1c}$ and $R^{2c}$ are both hydrogen or one of them is hydrogen and the other is alkanoyl or alkenoyl; and $R^{1d}$ and $R^{2d}$ are groups in which at least one of the hydrogen atoms of the above-described $R^{1c}$ and $R^{2c}$ is substituted with t-$BuMe_2Si$ (wherein t-$BuMe_2Si$ represents tert-butyldimethylsilyl).}

Step 4

Compound (Ie) can be obtained by allowing Compound (Id) to react with tert-butyldimethylsilyl chloride in the presence of a base. Chloroform, dichloromethane, ether, tetrahydrofuran, acetone, dimethylformamide, acetonitrile and the like may be used as the solvent either alone or as a mixture thereof. Amines (e.g., pyridine, imidazole, triethylamine, diisopropylethylamine and the like) may be used as the base. Tert-butyldimethylsilyl chloride is used in an amount of generally 1 equivalent or more, preferably 1 to 10 equivalents, based on Compound (Id). The base is used in an amount of generally 1 equivalent or more, preferably 1 to 5 equivalents, based on tert-butyldimethylsilyl chloride. The reaction is carried out generally at 0 to 50° C. for 10 minutes to 24 hours.

In the production of Compound (I), conversion of the functional group of $R^1$, $R^2$, $R^3$, X or Y can be effected not only by the aforementioned steps but also by known methods [for example, Comprehensive Organic Transformations, R. C. Larock, (1989)].

Isolation and purification of the products of the aforementioned methods can be effected by carrying out optional combinations of techniques generally used in organic syntheses (e.g., filtration, extraction, washing, drying, concentration, crystallization, various types of chromatography and the like). The intermediates may be used in the subsequent reactions without purification.

If it is desirable to obtain a salt of Compound (I), the salt of Compound (I) can be purified as such when it can be obtained; or, when the compound is obtained in its free form, its salt can be formed by dissolving or suspending it in an appropriate solvent and adding an acid or base thereto.

Also, Compound (I) or its pharmacologically acceptable salts may exist in the form of addition products with water or various solvents, and these addition products are also included in the present invention.

Examples of Compound (I) are shown in Table 1.

TABLE 1 (1)

Examples of Compound (I)

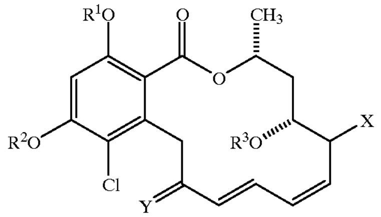

| Compound | $R^1$,$R^2$ | $R^3$ | X | Y |
|---|---|---|---|---|
| 1 | H | HCO | Cl | O |
| 2 | H | H | Cl | O |
| 3 | H | H | Br | O |
| 4 | H | $Z^a$ | Cl | O |
| 5 | $CH_3CO$ | $CH_3CO$ | Cl | O |
| 6 | $CH_3CO$ | HCO | Cl | O |
| 7 | $CH_3CO$ | $Z^a$ | Cl | O |
| 8 | H | | — | NOH |
| 9 | H | | — | $NOCH_3$ |
| 10 | $(CH_3)_3C(CH_3)_2Si$ | | — | O |
| 11 | $(CH_3)_3C(CH_3)_2Si$ | | — | NOH |
| 12 | $(CH_3)_3C(CH_3)_2Si$ | | — | $NOCH_2OCH_3$ |
| 13 | H | | — | $NOCH_2OCH_3$ |
| 14 | H | | — | $NO(CH_2)_3N_3$ |
| 15 | $CH_3(CH_2)_{14}CO$ | HCO | Cl | O |
| 16 | $CH_3(CH_2)_{14}CO$ | $Z^a$ | Cl | O |

$Z^a$ =

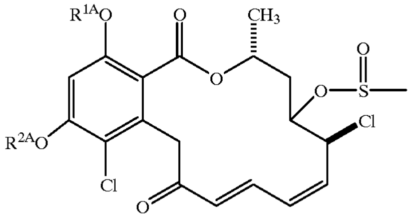

(wherein $R^{1A}$ and $R^{2A}$ have the same meaning as $R^1$ and $R^2$, respectively.)

In the definition of $R^3$ and X, "—" represents a single bond formed by combining $R^3$ and X with each other.

TABLE 1 (2)

Examples of Compound (I)

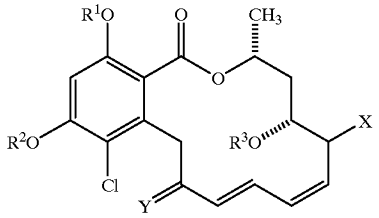

| Compound | $R^1$,$R^2$ | $R^3$ | X | Y |
|---|---|---|---|---|
| 17 | $CH_3(CH_2)_{14}CO$ | H | Cl | O |
| 18 | $CH_3(CH_2)_{14}CO$ | $CH_3CO$ | Cl | O |
| 19 | $CH_3(CH_2)_{14}CO$ | H | Br | O |
| 20 | $CH_3(CH_2)_{14}CO$ | $CH_3CO$ | Br | O |
| 21 | $CH_3(CH_2)_{14}CO$ | $CH_3(CH_2)_{14}CO$ | Cl | O |
| 22 | $(CH_3)_3C(CH_3)_2Si$ | | — | $NO(CH_2)_6Pht$ |
| 23 | H | | — | $NO(CH_2)_6Pht$ |
| 24 | H | | — | $NO(CH_2)_6N_3$ |
| 25 | H | | — | $NO(CH_2)_5CO_2C(CH_3)_3$ |
| 26 | H | | — | $NO(CH_2)_5CO_2(CH_2)_2Si(CH_3)_3$ |
| 27 | H | | — | $NO(CH_2)_5NHCO_2CH_2CH{=}CH_2$ |
| 28 | H | | — | $NO(CH_2)_5CO_2H$ |
| 29 | H | | — | $NOCH_2CO_2H$ |

In the definition of $R^3$ and X, "—" represents a single bond formed by combining $R^3$ and X with each other.

In the definition of Y, "Pht" represents a phthalimido group.

TABLE 1 (3)

Examples of Compound (I)

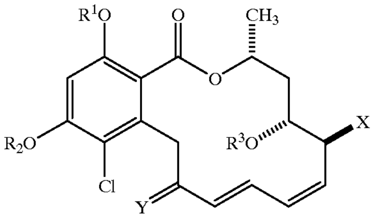

| Compound | —$R^1$,—$R^2$ | —$R^3$ | —X | =Y |
|---|---|---|---|---|
| 30 | —H | | — | $=NOCH_2CON(CH_3)_2$ |
| 31 | —H | | — | $=NO(CH_2)_3OH$ |
| 32 | $—CO(CH_2)_{14}CH_3$ | | — | $=NOCH_3$ |
| 33 | —H | —H | —Cl | $=NOCH_3$ |
| 34 | —H | —H | —Br | $=NOCH_3$ |
| 35 | —H | —CHO | —Cl | $=NOCH_3$ |
| 36 | —H | —H | —Cl | $=NOCH_2CON(CH_3)_2$ |

In the definition of $R^3$ and X, "—" represents a e bond formed by combining $R^3$ and X with each other.

BEST MODE OF CARRYING OUT THE INVENTION

Next, pharmacological activities of typical examples of Compound (I) are described by the following test examples.

Test Example 1

Inhibition Test of Intracellular Tyrosine Kinase

SR-3Y1 cells were cultured at 37° C. for 15 hours in an atmosphere of 5% carbon dioxide, using Dulbecco's modified Eagle's medium (DMEM) containing 10% fetal calf serum (FCS), to which each radicicol derivative to be tested has been added in varied concentration. The thus cultured cells were lysed at 4° C. for 20 minutes in a cooled buffer solution for lysis use (50 mM Tris HCl, pH 7.5, 150 mM NaCl, 1% Triton X-100, 0.1% SDS, 1% sodium deoxycholate, 2 mM EDTA, 1 mM PMSF, 20 μM leupeptin, 0.15 unit/ml aprotinin, 1 mM $Na_3VO_4$) and then centrifuged at 20,000 g for 30 minutes. After measuring protein concentration in the resulting supernatant fluid, samples were adjusted to the same protein quantity per lane to carry out separation of protein by SDS-PAGE. The thus separated protein samples were transferred onto a nitrocellulose membrane to which were subsequently added a mouse polyclonal phosphotyrosine antibody MX-pTYR (Kyowa Medex Co., Ltd.) as a first antibody and a horseradish peroxidase-conjugated mouse IgG antibody (BIO-RAD Co.) as a second antibody, thereby effecting their reactions with the protein samples on the membrane. Detection was carried out using ECL reagent (Amersham Co.), and the amount of tyrosine-phosphorylated protein was determined by scanning the density of banks obtained on an X-ray film. The activity of radicicol derivative to inhibit tyrosine phosphorylation can be shown as a concentration ($IC_{50}$) of each derivative by which the ratio of tyrosine-phosphorylated protein is reduced to half in comparison with a control to which the drug is not added.

The results are shown in Table 2.

TABLE 2

Inhibitory Activity of Intracellular Tyrosine Kinase

| Compound | $IC_{50}$ (μM) |
|---|---|
| Radicicol | 0.18 |
| 8 | 0.02 |
| 9 | <0.05 |

TABLE 2-continued

| Inhibitory Activity of Intracellular Tyrosine Kinase | |
|---|---|
| Compound | $IC_{50}$ ($\mu$M) |
| 10 | 0.15 |
| 11 | 0.02 |
| 14 | <0.05 |

According to Table 2, Compound (I) shows clearly strong action to inhibit intracellular tyrosine kinase activity in comparison with radicicol and therefore is useful as a tyrosine kinase inhibitor.

Test Example 2

Cell Growth Inhibition Test on HeLa $S_3$ Cells

HeLa $S_3$ cells which have been adjusted to $3.0\times10^4$ cells/ml with MEM medium (manufactured by Nissui Pharmaceutically containing 10% fetal calf serum and 2 mM glutamic acid were dispensed in 0.1 ml/well portions into a 96 well microtiter plate. The cells were cultured at 37° C. for 20 hours in a carbon dioxide gas incubator, the culture supernatant was removed and then the plate was washed once with physiological saline. Next, 0.1 ml of the medium containing each test compound was added to each well, and the cells were cultured at 37° C. for 72 hours in the carbon dioxide gas incubator. After removing the culture supernatant, 0.1 ml of the medium containing 0.02% Neutral Red was added to each well, and the cells were stained at 37° C. for 1 hour in the carbon dioxide gas incubator. After removing the culture supernatant, the plate was washed once with physiological saline, the pigment was extracted with 0.001 N hydrochloric acid/30% ethanol and then absorption at 550 nm was measured by a microplate reader. The concentration of each test compound which inhibits 50% of the cell growth ($IC_{50}$) was calculated by comparing the absorption of un-treated cells with that of the cells treated with known concentration of each sample.

The results are shown in Table 3.

TABLE 3

| Cell Growth Inhibition Activity upon HeLa $S_3$ Cells | |
|---|---|
| Compound | $IC_{50}$ ($\mu$M) |
| Radicicol | 6.7 |
| 4 | 6.0 |
| 6 | 5.0 |
| 7 | 1.5 |
| 8 | 0.09 |
| 9 | 0.05 |
| 10 | 3.2 |
| 11 | 0.12 |
| 13 | 0.02 |
| 14 | 0.05 |

According to Table 3, Compound (I) shows a cell growth inhibition activity upon HeLa $S_3$ cells, which is stronger than that of the known radicicol and therefore is useful as an antitumor agent.

Test Example 3

Antitumor Test on P388 Leukemia

The ascitic fluid was collected from the abdominal cavity of P388 ascites-induced mouse (DBA/2) 7 days after the transplantation. The number of P388 cells in the ascitic fluid was counted to prepare a tumor cell suspension of $5\times10^6$ cells/ml using sterilized physiological saline, and its 0.2 ml portion (containing $1\times10^6$ cells) was transplanted into the abdominal cavity of $CDF_1$ mice having 20 to 25 g in body weight. Each of the test compounds was dissolved in physiological saline containing polyoxyethylene sorbitan monolaurate, its 0.2 ml portion was administered into the abdominal cavity of $CDF_1$ mice of 5 animals per group 24 hours after the tumor transplantation and then their survival days were observed for 30 days. Effects of the test compounds were judged by the ratio of average survival days in the test compound-administered group to that in the control group (un-treated group) (increased life span, ILS %).

The results are shown in Table 4.

TABLE 4

| Antitumor Activity upon P388 Leukemia | |
|---|---|
| Compound | ILS (%) |
| Radicicol | 27 |
| 1 | 38 |
| 3 | 46 |
| 4 | 42 |

According to Table 4, Compound (I) shows excellent increased life span in comparison with radicicol and therefore is useful as an antitumor agent.

Test Example 4

Antitumor Test on Sarcoma 180 Solid Tumors

Seven days after transplantation of $5\times10^6$ of sarcoma 180 cells into the abdominal cavity of a ddY mouse, the cells were collected from the ascitic fluid, washed once with sterilized physiological saline and then made into a cell suspension of $5\times10^7$ cells/ml using sterilized physiological saline. A 0.1 ml portion of the cell suspension was transplanted under the skin of the right side axillary part of ddY mice of 20±2 g in body weight and, after 24 hours of the tumor transplantation, 0.1 to 0.2 ml of each test compound dissolved in physiological saline or polyoxyethylene sorbitan monolaurate-containing physiological saline was administered by intravenous injection to ddY mice of 5 animals per group. The major axis (a) and the minor axis (b) of each tumor 7 days after the transplantation were measured to calculate the tumor volume as an $a\times b^2/2$ value. Antitumor activity of each test compound was expressed by the ratio (T/C) of the tumor volume (T) of the test compound-administered group to the tumor volume (C) of the control group in which the drug was not administered.

The results are shown in Table 5.

TABLE 5

| Antitumor Activity upon Sarcoma 180 Solid Tumor | |
|---|---|
| Compound | T/C (%) |
| Radicicol | 88 |
| 1 | 51 |
| 2 | 50 |
| 4 | 39 |

According to Table 5, Compound (I) shows excellent antitumor activity in comparison with radicicol and therefore is useful as an antitumor agent.

Test Example 5

Antibacterial Activity Test the antibacterial activity was measured by an agar dilution method using a medium (pH 7) which has been prepared by dissolving 3 g of Bacto-Tryptone (manufactured by Difco), 3 g of meat extract, 1 g of yeast extract, 1 g of flucose and 16 g of agar in 1 l of water. The antibacterial activity was expressed by minimum growth inhibition concentration (MIC).

The results are shown in Table 6.

TABLE 6

| Compound | Antibacterial Activity Minimum Growth Inhibition Concentration (μg/ml) CA | BS | EH |
|---|---|---|---|
| Radicicol | 20 | 83 | — |
| 1 | — | 83 | — |
| 3 | — | 83 | — |
| 4 | 2.6 | 1.3 | 2.6 |
| 9 | 6.5 | 52 | — |

CA: *Candida albicans* ATCC 10231
BS: *Eacillus subtilis* No. 10707
EH: *Enterococcus hirae* ATCC 10541

According to Table 6, Compound (I) shows antibacterial activity and therefore is useful as an antibacterial agent.

Test Example 6

T Cell Growth Inhibition Test by Mixed Mouse Lymphocyte Culture Reaction

The spleen was excised aseptically from an AKR mouse (Japan SLC Co., Ltd.) and made into a single cell suspension. The suspension was mixed with mitomycin C (MMC) (Kyowa Hakko Kogyo Co., Ltd.) (final concentration, 50 μg/ml) and cultured at 37° C. for 30 minutes. After the culturing, the cells were washed three times with a solution (HBSS) prepared by adding 2.5% fetal calf serum (FCS, Gibco Co.) to Hanks' balanced salt solution (Gibco Co.) and then adjusted to a density of $1\times10^7$ cells/ml.

A 50 μl portion of B10.BR mouse (Japan SLC Co., Ltd.) lymph node cell suspension (containing $1.5\times10^5$ cells), 50 μl of AKR mouse spleen cell suspension (containing $5\times10^5$ cells) and 100 μl of radicicol solution having each test concentration were added to each well of a 96 well microtiter plate and cultured at 37° C. for 72 hours in a $CO_2$ incubator. A 1.0 μCi portion of [$^3$H]-thymidine was added 18 hours before the completion of the culturing. After completion of the culturing, the cells were trapped on a filter paper using a cell harvester and dried, and then a toluene scintillator was added thereto to measure the amount of radioactivity of [$^3$H]-thymidine incorporated into cells using a scintillation counter (test group). As a control group, the same culturing was carried out without adding the solution of Compound (I) and then the amount of radioactivity of [$^3$H]-thymidine incorporated into cells was measured. The T cell growth inhibition ratio was calculated based on the following formula, from which the concentration of each test compound that inhibits 50% of the growth ($IC_{50}$was calculated.

$$\text{T Cell Growth Inhibition Ratio (\%)} = \frac{\text{Radioactivity in Control Group} - \text{Radioactivity in Test Group}}{\text{Radioactivity in Control Group} - \left[\text{Radioactivity in MMC-Treated AKR Mouse} + \text{Radioactivity in B10.BR Mouse Before Stimulation}\right]}$$

(In the above formula, the radioactivity in MMC-treated AKR mouse means the radiation dose of [$^3$H]-thymidine incorporated into MMC-treated AKR mouse spleen cells, and the radioactivity in B10.BR mouse means the radiation dose of [$^3$H]-thymidine incorporated into B10.BR mouse lymph node cells.)

The results are shown in Table 7.

TABLE 7

T Cell Growth Inhibition Ratio (%) by Mixed Mouse Lymphocyte Culture Reaction

| Compound | $IC_{50}$ (μM) |
|---|---|
| Radicicol | 0.15 |
| 3 | 0.3 |
| 8 | 0.01 |
| 9 | 0.02 |
| 19 | 0.15 |

According to Table 7, Compound (I) inhibited growth of T cells by the mixed mouse lymphocyte culture reaction, thus showing clear immunosuppression action. In addition, the suppression action was superior to that in the prior art of radicicol.

Compound (I) or a pharmacologically acceptable salt thereof is applied by oral or parenteral administration as it is or in the form of a pharmaceutical composition. Examples of the dosage form of such a pharmaceutical composition include tablets, pills, powders, granules, capsules, suppositories, injections, drip infusions and the like.

These dosage forms can be prepared by employing generally known methods and may contain various fillers, lubricants, binders, disintegrators, suspending agents, tonicity agents, emulsifying agents, absorption enhancers and the like.

Examples of carriers to be used in the pharmaceutical composition include water, distilled water for injection use, physiological saline, glucose, fructose, sucrose, mannitol, lactose, starch, corn starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resin, sorbitan fatty acid ester, glycerol fatty acid ester and the like, which may be optionally selected in response to the type of the pharmaceutical preparation.

Although the dosage and the number of administration times for the aforementioned purposes may vary depending on the intended therapeutic effect, administration method, treating period, age, body weight and the like, it may be administered generally in a dose of 0.01 to 5 mg/kg per day per adult.

The mode of the present invention will be described with reference to the following examples and reference examples. In this connection, structural formula of each compound is shown in Table 1 above.

EXAMPLE 1

Compound 1

A 1 ml portion of phosphorus oxychloride was added dropwise to 5 ml of dimethylformamide which was cooled in an ice bath. After 30 minutes of stirring at room temperature, the thus prepared solution was slowly added to a dimethylformamide solution (20 ml) of radicicol (2 g) while stirring in an ice bath, and the mixture was then stirred at room temperature for 24 hours. The reaction solution was diluted with ethyl acetate (200 ml), washed three times with water and then dried with anhydrous sodium sulfate. The solvent was evaporated under reduced pressure and the resulting residue was purified by silica gel column chromatography (2% methanol/chloroform) to obtain 1.4 g of Compound 1.

$^1$HMR($CD_3OD$) δ (ppm): 8.00 (1H, s), 7.14 (1H, ddd, 1.0, 11.2, 16.1 Hz), 6.44 (1H, s), 6.16 (1H, t, 10.8 Hz), 5.95 (1H, d, 16.1 Hz), 5.68 (1H, t, 10.0 Hz), 5.32 (1H, m), 5.25 (1H, m), 5.20 (1H, dd, 5.6, 10.0 Hz), 4.10 (1H, d, 16.1 Hz), 3.65 (1H, d, 16.1 Hz), 1.97 (1H, m), 1.42 (3H, d, 6.3 Hz) FAB-MS m/z: 429 $[M+H]^+$

EXAMPLE 2

Compound 2

A 1.3 ml portion of concentrated hydrochloric acid (36%) was added dropwise to a dioxane solution (70 ml) of radicicol (2 g) while cooling in an ice bath, and the mixture was stirred at room temperature for 6 hours. The reaction solution was mixed with water (100 ml), carefully neutralized with saturated sodium bicarbonate aqueous solution while cooling in an ice bath and then extracted three times with ethyl acetate (150 ml). The extract was dried with anhydrous sodium sulfate, the solvent was evaporated under reduced pressure and then the resulting residue was purified by silica gel column chromatography (2% methanol/chloroform) to obtain 1 g of Compound 2.

$^1$H-NMR ($CD_3OD$) δ (ppm): 7.25 (1H, ddd, 1.0, 11.3, 16.4 Hz), 6.50 (1H, s), 6.21 (1H, dt, 1.0, 11.7 Hz), 5.99 (1H, d, 16.4 Hz), 5.79 (1H, dt, 1.0, 11.7 Hz), 5.42 (1H, m), 5.17 (1H, ddd, 1.0, 5.9, 11.7 Hz), 4.25 (1H, d, 16.4 Hz), 4.03 (1H, dd, 5.9, 8.1 Hz), 3.70 (1H, d, 16.4 Hz), 2.07 (1H, ddd, 1.2, 6.8, 15.1 Hz), 1.93 (1H, ddd, 3.7, 8.1, 15.1 Hz), 1.46 (3H, d, 6.3 Hz) FAB-MS m/z: 401 $[M+H]^+$

EXAMPLE 3

Compound 3

A 1.0 ml portion of concentrated hydrobromic acid (47%) was added dropwise to a dioxane solution (50 ml) of radicicol (2.5 g) while cooling in an ice bath, and the mixture was stirred at room temperature for 2 hours. The reaction solution was mixed with water (100 ml), carefully neutralized with saturated sodium bicarbonate aqueous solution while cooling in an ice bath and then extracted three times with ethyl acetate (150 ml). The extract was dried with anhydrous sodium sulfate, the solvent was evaporated under reduced pressure and then the resulting residue was purified by silica gel column chromatography (2% methanol/chloroform) to obtain 1.7 g of Compound 3.

$^1$H-NMR ($CD_3OD$) δ (ppm): 7.28 (1H, dd, 10.8, 16.0 Hz), 6.51 (1H, s), 6.13 (1H, t, 10.8 Hz), 6.00 (1H, d, 16.0 Hz), 5.96 (1H, t, 10.8 Hz), 5.40 (1H, m), 5.33 (1H, dd, 5.2, 10.8 Hz), 4.24 (1H, d, 16.1 Hz), 4.18 (1H, m), 3.71 (1H, d, 16.1 Hz), 2.08 (1H, m), 1.92 (1H, m), 1.45 (3H, d, 6.4 Hz) FAB-MS m/z: 445, 447 $[M+H]^+$

EXAMPLE 4

Compound 4

A 0.5 ml portion of thionyl chloride was added dropwise to a dimethylformamide solution (7.5 ml) of radicicol (1.4 g) while cooling in an ice bath, and the mixture was stirred at room temperature for 12 hours. The reaction solution was diluted by adding ethyl acetate (100 ml) and washed three times with water. This was dried with anhydrous sodium sulfate, the solvent was evaporated under reduced pressure and then the resulting residue was purified by silica gel column chromatography (4% methanol/chloroform) to obtain 1.0 g of Compound 4.

$^1$H-NMR ($CD_3OD$) δ (ppm): 7.15 (2H, dd, 10.8, 16.1 Hz), 6.52 (2H, s), 6.27 (2H, t, 10.8 Hz), 6.05 (2H, d, 16.1 Hz), 5.73 (2H, t, 10.8 Hz), 5.39 (2H, m), 5.35 (2H, m), 4.88 (2H, m), 4.28 (2H, d, 16.4 Hz), 3.74 (2H, d, 16.4 Hz), 2.27 (2H, m), 2.10 (2H, m), 1.50 (6H, d, 6.3 Hz) FAB-MS m/z: 847 $[M+H]^+$

EXAMPLE 5

Compound 5

A 0.75 ml portion of acetic anhydride was added to an anhydrous pyridine solution (1 ml) of Compound 2 (170 mg), and the mixture was stirred at room temperature for 10 hours. The reaction solution was diluted with 20 ml of ethyl acetate and then washed with water, dilute hydrochloric acid aqueous solution and saturated sodium bicarbonate aqueous solution in that order. This was dried with anhydrous sodium sulfate, the solvent was evaporated under reduced pressure and then the resulting residue was purified by silica gel column chromatography (2:1 n-hexane/ethyl acetate) to obtain 125 mg of Compound 5.

$^1$H-NMR ($CDCl_3$) δ (ppm): 7.06 (1H, s), 6.93 (1H, dd, 11.2, 16.3 Hz), 6.12 (1H, t, 11.2 Hz), 6.04 (1H, d, 16.1 Hz), 5.73 (1H, t, 11.2 Hz), 5.40 (1H, m), 5.14 (1H, t, 8.0 Hz), 5.00 (1H, ddd, 1.1, 8.0, 11.2 Hz), 4.41 (1H, d, 16.3 Hz), 3.96 (1H, d, 16.3 Hz), 2.35 (3H, s), 2.34 (3H, s), 2.21 (1H, dd, 8.7, 15.4 Hz), 2.04 (1H, ddd, 3.3, 8.7, 15.4 Hz), 1.96 (3H, s), 1.54 (3H, d, 6.3 Hz) FAB-MS m/z: 527 $[M+H]^+$

EXAMPLE 6

Compound 6

Acetic anhydride (1 ml) was added to a pyridine solution (1 ml) of Compound 1 (166 mg), and the mixture was stirred at room temperature for 13 hours. The reaction solution was diluted with water and then extracted with ethyl acetate (50 ml×3). The extract was washed with dilute hydrochloric acid aqueous solution, saturated sodium bicarbonate aqueous solution and saturated sodium chloride aqueous solution in that order. This was dried with anhydrous sodium sulfate, the solvent was evaporated under reduced pressure and then the resulting residue was purified by silica gel column chromatography (2:1 n-hexane/ethyl acetate) to obtain 174 mg of Compound 6.

$^1$H-NMR ($CDCl_3$) δ (ppm): 7.99 (1H, s), 7.07 (1H, s), 6.93 (1H, dd, 11.1, 16.3 Hz), 6.14 (1H, t, 11.1 Hz), 6.04 (1H, d, 16.3 Hz), 5.75 (1H, t, 11.1 Hz), 5.43 (1H, m), 5.34 (1H, t, 7.5 Hz), 5.05 (1H, dd, 7.5, 11.1 Hz), 4.31 (1H, d, 16.2 Hz), 3.96 (1H, d, 16.2 Hz), 2.35 (3H, s), 2.34 (3H, s), 2.14 (1H, m), 2.06 (1H, m), 1.57 (3H, d, 6.4 Hz) FAB-MS m/z: 513 $[M+H]^+$

EXAMPLE 7

Compound 7

Acetic anhydride (0.5 ml) was added to a pyridine solution (0.5 ml) of Compound 4 (30 mg), and the mixture was stirred at room temperature for 13 hours. The solvent was evaporated under reduced pressure and the resulting residue was purified by silica gel column chromatography (1:1 n-hexane/ethyl acetate) to obtain 30 mg of Compound 7.

$^1$H-NMR ($CDCl_3$) δ (ppm): 7.06 (2H, s), 6.88 (2H, dd, 11.0, 15.9 Hz), 6.17 (2H, t, 10.8 Hz), 6.05 (2H, d, 16.3 Hz), 5.67 (2H, t, 10.4 Hz), 5.45 (2H, m), 5.05 (2H, dd, 7.8, 9.7 Hz), 4.82 (2H, dd, 8.5, 8.4 Hz), 4.30 (2H, d, 15.8 Hz), 3.95 (2H, d, 15.8 Hz), 2.338 (6H, s), 2.337 (6H, s), 2.25 (2H, m), 2.06 (2H, m), 1.54 (6H, d, 6.4 Hz) FAB-MS m/z: 1015 $[M+H]^+$

EXAMPLE 8

Compound 8

Hydroxylamine hydrochloride (20 mg) was added to a pyridine solution (2 ml) of radicicol (42 mg), and the mixture was stirred at 50° C. for 8 hours. The solvent was evaporated under reduced pressure and the resulting residue was purified by silica gel column chromatography (25:1 chloroform/methanol) to obtain 10 mg of Compound 8. Compound 8 thus obtained was identified by $^1$H-NMR to find that it was a mixture (about 3:1) of isomers due to the oxime hydroxyl group.

$^1$H-NMR ($CD_3OD$) δ (ppm): 7.22 (1H, dd, 11.3, 16.2 Hz), 7.12 (0.5H, dd, 11.2, 16.1 Hz), 6.83 (1.5H, d, 16.2 Hz), 6.43 (1H, s), 6.42 (0.5H, s), 6.16 (1H, t, 11.3 Hz), 6.11 (0.5H, t, 11.2 Hz), 5.58 (1H, dd, 3.6, 11.3 Hz), 5.46 (0.5H, dd, 3.4, 11.2 Hz), 5.30 (1.5H, m), 4.79 (0.5H, d, 16.3 Hz), 4.72 (0.5H, d, 16.3 Hz), 3.91 (1H, d, 16.1 Hz), 3.81 (1H, d, 16.1 Hz), 3.35 (1.5H, m), 3.02 (1.5H, m), 2.97 (0.5H, m), 2.42 (1.5H, m), 1.60 (1.5H, m), 1.53 (3H, d, 6.6 Hz), 1.52 (1.5H, d, 7.7 Hz) FAB-MS m/z: 380 $[M+H]^+$

EXAMPLE 9

Compound 9

O-Methylhydroxylamine hydrochloride (100 mg) was added to a pyridine solution (1 ml) of radicicol (200 mg), and the mixture was stirred at 80° C. for 90 minutes. The solvent was evaporated under reduced pressure and the resulting residue was purified by silica gel column chromatography (1% methanol/chloroform) to obtain 34 mg of Compound 9.

$^1$H-NMR ($CD_3OD$) δ (ppm): 7.23 (1H, dd, 11.3, 16.2 Hz), 6.70 (1H, d, 16.2 Hz), 6.42 (1H, s), 6.14 (1H, t, 11.3 Hz), 5.58 (1H, dd, 3.6, 11.3 Hz), 5.30 (1H, m), 3.904 (1H, d, 16.1 Hz), 3.901 (3H, s), 3.80 (1H, d, 16.1 Hz), 3.33 (1H, m), 3.01 (1H, m), 2.42 (1H, ddd, 3.5, 3.5, 14.5 Hz), 1.59 (1H, ddd, 4.1, 9.0, 14.5 Hz), 1.52 (3H, d, 6.5 Hz) FAB-MS m/z: 394 $[M+H]^+$

EXAMPLE 10

Compound 10

A dimethylformamide solution (7.5 ml) of radicicol (500 mg) was cooled in an ice bath and mixed with dimethylformamide solutions (2.5 ml) of imidazole (700 mg) and t-butyldimethylsilane chloride (1.1 g) in that order, and the mixture was stirred at room temperature for 12 hours. The reaction solution was diluted by adding ethyl acetate (50 ml) and then washed twice with water. This was dried with anhydrous sodium sulfate, the solvent was evaporated under reduced pressure and then the resulting residue was purified by silica gel column chromatography (3:1 n-hexane/ethyl acetate) to obtain 902 mg of Compound 10.

$^1$H-NMR ($CDCl_3$) δ (ppm): 7.58 (1H, dd, 10.8, 16.2 Hz), 6.39 (1H, s), 6.13 (1H, ddd, 1.1, 10.8, 10.8 Hz), 6.04 (1H, d, 16.2 Hz), 5.78 (1H, dd, 3.5, 10.8 Hz), 5.32 (1H, m), 3.89 (1H, d, 16.3 Hz), 3.70 (1H, d, 16.3 Hz), 3.40 (1H, ddd, 1.9, 1.9, 3.4 Hz), 3.02 (1H, ddd, 1.9, 2.3, 9.4 Hz), 2.44 (1H, ddd, 3.2, 3.2, 14.4 Hz), 1.54 (3H, d, 6.6 Hz), 1.50 (1H, m), 1.00 (9H, s), 0.94 (9H, s), 0.24 (3H, s), 0.22 (3H, s), 0.21 (3H, m), 0.20 (3H, s) FAB-MS m/z: 593 $[M+H]^+$

EXAMPLE 11

Compound 11

Pyridine (0.1 ml) and hydroxylamine hydrochloride (240 mg) were added to a dichloromethane solution (5 ml) of Compound 10 (319 mg), and the mixture was stirred at 70° C. for 30 hours. The reaction solution was cooled to room temperature, diluted with chloroform and then washed with dilute hydrochloric acid aqueous solution, saturated sodium bicarbonate aqueous solution and saturated sodium chloride aqueous solution in that order. This was dried with anhydrous sodium sulfate, the solvent was evaporated under reduced pressure and then the resulting residue was purified by silica gel column chromatography (1:1 n-hexane/ethyl acetate) to obtain 18 mg of Compound 11. Compound 11 thus obtained was identified by $^1$H-NMR to find that it was a mixture (about 1:1) of isomers due to the oxime hydroxyl group.

$^1$H-NMR ($CDCl_3$) δ (ppm): 7.24 (1H, dd, 11.3, 16.1 Hz), 7.13 (1H, dd, 11.2, 16.0 Hz), 6.87 (1H, d, 16.1 Hz), 6.37 (1H, s), 6.36 (1H, s), 6.20 (1H, d, 16.0 Hz), 6.14 (1H, t, 11.3 Hz), 6.08 (1H, t, 11.2 Hz), 5.65 (1H, dd, 3.0, 11.3 Hz), 5.53 (1H, dd, 3.1, 11.2 Hz), 5.26 (2H, m), 4.85 (1H, d, 16.3 Hz), 3.91 (1H, d, 16.2 Hz), 3.60 (1H, d, 16.2 Hz), 3.39 (2H, m), 3.01 (1H, d, 16.3 Hz), 2.98 (2H, m), 2.42 (2H, m), 1.56 (3H, d, 6.5 Hz), 1.54 (3H, d, 6.5 Hz), 1.49 (2H, m), 1.00 (18H, s), 0.943 (9H, s), 0.942 (9H, s), 0.23 (6H, s), 0.212 (6H, s), 0.209 (6H, s), 0.20 (6H, s) FAB-MS m/z: 608 $[M+H]^+$

EXAMPLE 12

Compound 12

Diisopropylethylamine (160 μl) and chloromethyl methyl ether (75 μl) were added in that order at 0° C. to a dichloromethane solution (1 ml) of Compound 11 (100 mg), and the mixture was stirred at 0° C. for 7 hours. The solvent was evaporated under reduced pressure and the resulting residue was purified by silica gel column chromatography (5:1 n-hexane/ethyl acetate) to obtain 58 mg of Compound 12. Compound 12 thus obtained was identified by $^1$H-NMR to find that it was a mixture (about 1:1) of isomers due to the oxime hydroxyl group.

$^1$H-NMR ($CDCl_3$) δ (ppm): 7.24 (1H, dd, 11.2, 16.1 Hz), 7.12 (1H, dd, 11.2, 16.1 Hz), 6.81 (1H, d, 16.1 Hz), 6.36 (2H, s), 6.12 (1H, ddd, 2.0, 11.2, 11.2 Hz), 6.07 (1H, ddd, 1.5, 11.2, 11.2 Hz), 5.66 (1H, dd, 2.9, 11.2 Hz), 5.52 (1H, dd, 3.2, 11.2 Hz), 5.28 (2H, m), 5.22 (2H, ABq, 7.3 Hz), 5.18 (2H, s), 4.81 (1H, d, 16.4 Hz), 3.97 (1H, d, 16.4 Hz), 3.59 (1H, d, 16.4 Hz), 3.50 (3H, s), 3.48 (3H, s), 3.37 (2H, m), 3.05 (1H, d, 16.4 Hz), 3.02–2.94 (2H, m), 2.45–2.39 (2H, m), 1.56 (3H, d, 7.8 Hz), 1.54 (3H, d, 6.6 Hz), 1.00 (18H, s), 0.943 (9H, s), 0.940 (9H, s), 0.23 (6H, s), 0.21 (6H, s), 0.204 (6H, s), 0.200 (6H, s) FAB-MS m/z: 652 $[M+H]^+$

EXAMPLE 13

Compound 13

A 1 M tetrahydrofuran solution (50 μl) of tetra-n-butylammonium fluoride was added to a tetrahydrofuran solution (0.5 ml) of Compound 12 (22 mg), and the mixture was stirred at room temperature for 2 hours. The reaction solution was diluted with ethyl acetate and then washed twice with water. This was dried with anhydrous sodium sulfate, the solvent was evaporated under reduced pressure and then the resulting residue was purified by silica gel column chromatography (2% methanol/chloroform) to obtain 11 mg of Compound 13. Compound 13 thus obtained was identified by $^1$H-NMR to find that it was a mixture (about 1:1) of isomers due to the oxime hydroxyl group.

$^1$H-NMR ($CD_3OD$) δ (ppm): 7.29 (1H, dd, 11.2, 16.1 Hz), 7.18 (1H, dd, 11.0, 16.1 Hz), 6.77 (1H, d, 16.1 Hz), 6.43 (2H, s), 6.17 (1H, t, 11.2 Hz), 6.16 (1H, d, 16.1 Hz), 6.13 (1H, t, 11.0 Hz), 5.61 (1H, dd, 3.4, 11.2 Hz), 5.50 (1H, dd, 3.4, 11.0 Hz), 5.30 (2H, m) 5.19 (2H, ABq, 7.3 Hz), 5.13 (2H, ABq, 7.1 Hz), 4.65 (1H, d, 16.6 Hz), 3.95 (1H, d, 16.4 Hz), 3.84 (1H, d, 16.4 Hz), 3.46 (1H, d, 16.6 Hz), 3.47 (3H, s), 3.43 (3H, s), 3.33 (1H, m), 3.30 (1H, m), 3.02 (1H, m), 2.97 (1H, m), 2.42 (2H, m), 1.68–1.58 (2H, m), 1.53 (3H, d, 7.8 Hz), 1.51 (3H, d, 6.6 Hz) FAB-MS m/z: 424 $[M+H]^+$

EXAMPLE 14

Compound 14

A pyridine solution (0.5 ml) of radicicol (36.4 mg) and O-(3-azidopropyl)hydroxylamine hydrochloride (20 mg) was stirred at room temperature for 14 hours. The solvent was evaporated under reduced pressure and the resulting residue was purified by silica gel column chromatography (1% methanol/chloroform) to obtain 29.3 mg of Compound 14.

$^1$H-NMR ($CD_3OD$) δ (ppm): 7.24 (1H, ddd, 1.0, 11.2, 16.1 Hz), 6.72 (1H, d, 16.1 Hz), 6.43 (1H, s), 6.15 (1H, ddd, 1.7, 11.2, 11.2 Hz), 5.59 (1H, dd, 3.7, 11.2 Hz), 5.30 (1H, m), 4.20 (2H, m), 3.92 (1H, d, 16.1 Hz), 3.81 (1H, d, 16.1 Hz), 3.42 (2H, t, 6.6 Hz), 3.34 (1H, m), 3.01 (1H, m), 2.42 (1H, ddd, 3.4, 3.4, 14.4 Hz), 1.96 (2H, m), 1.59 (1H, ddd, 3.9, 8.8, 14.4 Hz), 1.52 (3H, d, 6.4 Hz) FAB-MS m/z: 463 $[M+H]^+$

EXAMPLE 15

Compound 15

A methylene chloride solution (2 ml) of Compound 1 (60 mg) and 4-dimethylaminopyridine (40 mg) was cooled to 0° C., palmitoyl chloride (0.1 ml) was slowly added dropwise thereto and the resulting mixture was stirred at 0° C. for 30 minutes. The solvent was evaporated under reduced pressure and the resulting residue was purified by silica gel column chromatography (4:1 n-hexane/ethyl acetate) to obtain 92 mg of Compound 15.

$^1$H-NMR ($CDCl_3$) δ (ppm): 7.98 (1H, s), 7.03 (1H, s), 6.94 (1H, dd, 11.2, 16.3 Hz), 6.14 (1H, t, 11.2 Hz), 6.04 (1H, d, 16.3 Hz), 5.74 (1H, t, 11.2 Hz), 5.40 (1H, m), 5.32 (1H, br t, 7.6 Hz), 5.05 (1H, dd, 7.6, 11.2 Hz), 4.29 (1H, d, 16.3 Hz), 3.95 (1H, d, 16.3 Hz), 2.63–2.52 (4H, m), 2.14 (1H, dd, 7.6, 15.4 Hz), 2.05 (1H, m), 1.80–1.72 (4H, m), 1.55 (3H, d, 6.3 Hz), 1.43–1.26 (48H, m), 0.88 (6H, t, 6.7 Hz) FAB-MS m/z: 905 $[M+H]^+$

EXAMPLE 16

Compound 16

A methylene chloride solution (6 ml) of Compound 4 (96 mg) and 4-dimethylaminopyridine (126 mg) was cooled to 0° C., palmitoyl chloride was slowly added dropwise thereto and the resulting mixture was stirred at 0° C. for 2 hours. The solvent was evaporated under reduced pressure and then the resulting residue was purified by silica gel column chromatography (4:1 n-hexane/ethyl acetate) to obtain 130 mg of Compound 16.

$^1$H-NMR ($CDCl_3$) δ (ppm): 7.02 (2H, s), 6.88 (2H, m), 6.16 (1H, t, 10.8 Hz), 6.15 (1H, t, 10.8 Hz), 6.04 (1H, d, 16.2 Hz), 6.03 (1H, d, 16.2 Hz), 5.66 (1H, t, 10.8 Hz), 5.64 (1H, t, 10.8 Hz), 5.43 (2H, m), 5.06 (1H, dd, 6.0, 10.8 Hz), 5.02 (1H, dd, 6.8, 9.0 Hz), 4.80 (1H, br t, 8.8 Hz), 4.68 (1H, br t, 8.6 Hz), 4.29 (1H, d, 16.3 Hz), 4.27 (1H, d, 16.2 Hz), 3.95 (2H, d, 16.3 Hz), 2.60–2.52 (8H, m), 2.29–2.18 (2H, m), 2.06 (2H, m), 1.81–1.71 (8H, m), 1.522 (3H, d, 6.3 Hz), 1.517 (3H, d, 6.3 Hz), 1.43–1.21 (96H, m), 0.88 (12H, t, 6.8 Hz) FAB-MS m/z: 1801.9 $[M+H]^+$

EXAMPLE 17

Compound 17

Concentrated hydrochloric acid (36%, 0.5 ml) was added dropwise to a dioxane solution (5 ml) of Compound a (343 mg) obtained in Reference Example 1, and the mixture was stirred at room temperature for 30 minutes. The reaction solution was washed with water and dried with anhydrous sodium sulfate. The solvent was evaporated under reduced pressure and the resulting residue was purified by silica gel column chromatography (4:1 n-hexane/ethyl acetate) to obtain 96 mg of Compound 17.

$^1$H-NMR ($CDCl_3$) δ (ppm): 7.01 (1H, s), 6.95 (1H, dd, 11.1, 16.3 Hz), 6.21 (1H, t, 11.1 Hz), 6.03 (1H, d, 16.3 Hz), 5.77 (1H, t, 11.1 Hz), 5.51 (1H, m), 4.97 (1H, ddd, 1.0, 6.6, 11.1 Hz), 4.32 (1H, d, 16.2 Hz), 3.97 (1H, t, 6.6 Hz), 3.93 (1H, d, 16.2 Hz), 2.62–2.45 (4H, m), 2.12 (1H, m), 2.01 (1H, m), 1.79–1.69 (4H, m), 1.50 (3H, d, 6.3 Hz), 1.44–1.21 (48H, m), 0.88 (6H, t, 6.6 Hz) FAB-MS m/z: 877 $[M+H]^+$

EXAMPLE 18

Compound 18

A methylene chloride solution (4 ml) of Compound 17 (25 mg) was cooled to 0° C., pyridine (5 drops) and acetyl chloride (5 drops) were added dropwise thereto and the resulting mixture was stirred at 0° C. for 30 minutes. The solvent was evaporated under. reduced pressure and the-resulting residue was purified by silica gel column chromatography (5:1 n-hexane/ethyl acetate) to obtain 15 mg of Compound 18.

$^1$H-NMR ($CDCl_3$) δ (ppm): 7.02 (1H, s), 6.93 (1H, dd, 11.2, 16.4 Hz), 6.12 (1H, t, 11.2 Hz), 6.03 (1H, d, 16.4 Hz), 5.73 (1H, t, 11.2 Hz), 5.38 (1H, m), 5.13 (1H, t, 8.0 Hz), 5.01 (1H, dd, 8.0, 11.2 Hz), 4.34 (1H, d, 16.4 Hz), 3.96 (1H, d, 16.4 Hz), 2.61–2.55 (4H, m), 2.20 (1H, m), 2.03 (1H, m), 1.95 (3H, s), 1.80–1.71 (4H, m), 1.53 (3H, d, 6.4 Hz), 1.43–1.26 (48H, m), 0.88 (6H, t, 6.6 Hz) FAB-MS m/z: 919 $[M+H]^+$

EXAMPLE 19

Compound 19

Concentrated hydrobromic acid (47%, 3 drops) was slowly added dropwise to a dioxane solution (5 ml) of Compound a (106 mg), see below, obtained in reference Example 1, and the mixture was stirred at room temperature for 30 minutes. The reaction solution was diluted with chloroform and washed with water. This was dried with anhydrous sodium sulfate, the solvent was evaporated under reduced pressure and then the resulting residue was purified by silica gel column chromatography (3:1 n-hexane/ethyl acetate) to obtain 41 mg of Compound 19.

$^1$H-NMR ($CDCl_3$) δ (ppm): 7.03 (1H, s), 6.99 (1H, dd, 10.8, 16.1 Hz), 6.14 (1H, t, 10.8 Hz), 6.05 (1H, d, 16.1 Hz), 5.94 (1H, t, 10.8 Hz), 5.50 (1H, m), 5.10 (1H, dd, 5.9, 10.8 Hz), 4.29 (1H, d, 16.1 Hz), 4.13 (1H, br t, 5.9 Hz), 3.94 (1H, d, 16.1 Hz), 2.60–2.54 (4H, m), 2.13 (1H, dd, 6.9, 15.2 Hz), 2.00 (1H, m), 1.80–1.69 (4H, m), 1.50 (3H, d, 6.3 Hz), 1.44–1.26 (48H, m), 0.88 (6H, t, 6.6 Hz) FAB-MS m/z: 921, 923 $[M+H]^+$

EXAMPLE 20

Compound 20

Pyridine (5 drops) and acetic anhydride (3 drops) were added dropwise in that order to a methylene chloride solution (1 ml) of Compound 19, and the mixture was stirred at room temperature for 16 hours. The solvent was evaporated under reduced pressure and the resulting residue was purified by silica gel preparative thin layer chromatography (0.25 mm×10 cm×20 cm, 5:1 n-hexane/ethyl acetate) to obtain 4.3 mg of Compound 20.

$^1$H-NMR ($CDCl_3$) δ (ppm): 7.04 (1H, s), 6.97 (1H, dd, 10.7, 16.1 Hz), 6.05 (1H, t, 10.7 Hz), 6.04 (1H, d, 16.1 Hz), 5.89 (1H, t, 10.7 Hz), 5.38 (1H, m), 5.27 (1H, br t, 7.8 Hz), 5.09 (1H, dd, 7.8, 10.7 Hz), 4.32 (1H, d, 16.4 Hz), 3.96 (1H, d, 16.4 Hz), 2.63–2.56 (4H, m), 2.21 (1H, dd, 7.8, 14.4 Hz), 2.02 (1H, m), 1.976 (3H, s), 1.81–1.71 (4H, m), 1.53 (3H, d, 6.4 Hz), 1.47–1.23 (48H, m), 0.88 (6H, t, 6.8 Hz). FAB-MS m/z: 963, 965 $[M+H]^+$

EXAMPLE 21

Compound 21

4-Dimethylaminopyridine (300 mg) and palmitoyl chloride (1.0 ml) were added in that order to a methylene chloride solution (10 ml) of Compound 3 (250 mg), and the mixture was stirred at room temperature for 30 minutes. The solvent was evaporated under reduced pressure and then the resulting residue was purified by silica gel column chromatography (3:1 n-hexane/ethyl acetate) to obtain 130 mg of Compound 21.

$^1$H-NMR ($CDCl_3$) δ (ppm): 7.04 (1H, s), 6.97 (1H, dd, 11.0, 16.8 Hz), 6.04 (1H, t, 11.0 Hz), 6.00 (1H, d, 16.8 Hz), 5.89 (1H, t, 11.0 Hz), 5.38 (1H, m), 5.28 (1H, t, 7.6 Hz), 5.10 (1H, dd, 7.6, 11.0 Hz), 4.31 (1H, d, 16.1 Hz), 3.95 (1H, d, 16.1 Hz), 2.61–2.53 (6H, m), 2.22 (1H, dd, 7.8, 14.4 Hz), 2.01 (1H, m), 1.81–1.71 (6H, m), 1.53 (3H, d, 6.4 Hz), 1.43–1.26 (72H, m), 0.88 (6H, t, 6.8 Hz) FAB-MS m/z: 1160, 1162 $[M+H]^+$

EXAMPLE 22

Compound 22

Diethyl azodicarboxylate (0.1 ml) was added dropwise to a tetrahydrofuran solution (1.5 ml) of Compound 11 (250 mg), N-(6-hydroxyhexyl)phthalimide (244 mg) and triphenylphosphine (135 mg), and the mixture was stirred at room temperature for 21 hours. The solvent was evaporated under reduced pressure and then the resulting residue was purified by silica gel column chromatography (7.5:1 n-hexane/ethyl acetate) to obtain 49 mg of Compound 22.

$^1$H-NMR ($CDCl_3$) δ (ppm): 7.83 (2H, m), 7.71 (2H, m), 7.08 (1H, dd, 11.2, 16.1 Hz), 6.30 (1H, s), 6.27 (1H, d, 16.1 Hz), 6.18 (1H, dd, 10.5, 11.2 Hz), 5.48 (1H, dd, 3.2, 10.5 Hz), 5.24 (1H, m), 3.98 (1H, d, 16.1 Hz), 3.91 (2H, m), 3.69 (2H, m), 3.56 (1H, d, 16.1 Hz), 3.41 (1H, m), 2.96 (1H, m), 2.42 (1H, m), 1.83–1.37 (9H, m), 1.55 (3H, d, 6.5 Hz), 0.975 (9H, s), 0.973 (9H, s), 0.24 (3H, s), 0.22 (3H, s), 0.204 (3H, s), 0.197 (3H, s) FAB-MS m/z: 837 $[M+H]^+$

EXAMPLE 23

Compound 23

Tetra-n-butylammonium fluoride (1 M/tetrahydrofuran solution, 0.05 ml) was added dropwise to a tetrahydrofuran solution (1 ml) of Compound 22 (21.6 mg), and the mixture was stirred at room temperature for 10 minutes. The reaction solution was poured into saturated ammonium chloride aqueous solution and extracted three times with ethyl acetate. The extract was dried with anhydrous sodium sulfate, the solvent was evaporated under reduced pressure and then the resulting residue was purified by silica gel column chromatography (1% methanol/chloroform) to obtain 16 mg of Compound 23.

$^1$H-NMR ($CD_3OD$) δ (ppm): 7.79–7.71 (4H, m), 7.03 (1H, dd, 11.2, 16.1 Hz), 6.77 (1H, d, 16.1 Hz), 6.42 (1H, s)., 6.04 (1H, dd, 10.5, 11.2 Hz), 5.39 (1H, dd, 3.2, 10.5 Hz), 5.26 (1H, m), 3.93 (2H, m), 3.84 (1H, d, 16.1 Hz), 3.73 (1H, d, 16.1 Hz), 3.62 (2H, m), 3.23 (1H, m), 2.91 (1H, m), 2.39 (1H, m), 1.80–1.33 (9H, m), 1.47 (3H, d, 6.8 Hz) FAB-MS m/z: 609 $[M+H]^+$

EXAMPLE 24

Compound 24

O-(6-Azidohexyl)hydroxylamine hydrochloride (575 mg) was added to a pyridine solution (5 ml) of radicicol (900 mg), and the mixture was stirred at room temperature for 78 hours. The solvent was evaporated under reduced pressure and then the resulting residue was purified by silica gel column chromatography (1% methanol/chloroform) to obtain 319 mg of Compound 24.

$^1$H-NMR ($CD_3OD$) δ (ppm): 7.23 (1H, dd, 11.2, 16.1 Hz), 6.72 (1H, d, 16.1 Hz), 6.42 (1H, s), 6.15 (1H, dd, 10.5, 11.2 Hz), 5.58 (1H, 3.4, 10.5 Hz), 5.30 (1H, m), 4.19–4.08 (2H, m), 3.91 (1H, d, 16.1 Hz), 3.81 (1H, d, 16.1 Hz), 3.34 (1H, m), 3.01 (1H, m), 2.42 (1H, m), 1.77–1.65 (2H, m), 1.62–1.56 (9H, m), 1.52 (3H, d, 6.6 Hz) FAB-MS m/z: 505 $[M+H]^+$

EXAMPLE 25

Compound 25

O-[5-(Tert-butoxycarbonyl)pentyl]hydroxylamine hydrochloride (400 mg) was added to-a pyridine solution (3 ml) of radicicol (364 mg), and the mixture was stirred at room temperature for 19 hours and then at 60° C. for 2 hours. The solvent was evaporated under reduced pressure and then the resulting residue was purified by silica gel column chromatography (1% methanol/chloroform) to obtain 316 mg of Compound 25.

$^1$H-NMR ($CD_3OD$) δ (ppm): 7.23 (1H, dd, 11.3, 16.2 Hz), 6.71 (1H, dd, 16.2 Hz), 6.42 (1H, s), 6.15 (1H, dd, 10.3, 11.3 Hz), 5.58 (1H, dd, 3.4, 10.3 Hz), 5.30 (1H, m), 4.15–4.08 (2H, m), 3.91 (1H, d, 16.0 Hz), 3.81 (1H, d, 16.0 Hz), 3.33 (1H, m), 3.02 (1H, m), 2.42 (1H, m), 2.25–2.20 (2H, m), 1.75–1.34 (7H, m), 1.52 (3H, d, 6.5 Hz), 1.43 (9H, s) FAB-MS m/z: 550 $[M+H]^+$

EXAMPLE 26

Compound 26

O-[5-[[2-(Trimethylsilyl)ethyl]oxycarbonyl]pentyl]-hydroxylamine hydrochloride (915 mg) was added to a pyridine solution (2 ml) of radicicol (800 mg), and the mixture was stirred at room temperature for 22 hours. The solvent was evaporated under reduced pressure and then the resulting residue was purified by silica gel column chromatography (1% methanol/chloroform) to obtain 295 mg of Compound 26.

$^1$H-NMR ($CD_3OD$) δ (ppm): 7.23 (1H, dd, 11.2, 16.1 Hz), 6.71 (1H, d, 16.1 Hz), 6.42 (1H, s), 6.15 (1H, dd, 10.7, 11.2 Hz), 5.58 (1H, dd, 3.7, 10.7 Hz), 5.30 (1H, m), 4.19–4.13 (4H, m), 3.91 (1H, d, 16.1 Hz), 3.81 (1H, d, 16.1 Hz), 3.34 (1H, m), 3.01 (1H, m), 2.41 (1H, m), 2.33–2.29 (2H, m), 1.77–1.30 (7H, m), 1.52 (3H, d, 6.8 Hz), 1.00–0.95 (2H, m), 0.03 (9H, s) FAB-MS m/z: 594 [M+H]$^+$

EXAMPLE 27

Compound 27

O-[6-(Allyloxycarbonylamino)hexyl]hydroxylamine hydrochloride (116 mg) was added to a pyridine solution (3 ml) of radicicol (140 mg), and the mixture was stirred at room temperature for 79 hours. The solvent was evaporated under reduced pressure and then the resulting residue was purified by silica gel column chromatography (1% methanol/chloroform) to obtain 156 mg of Compound 27.

$^1$H-NMR ($CD_3OD$) δ (ppm): 7.23 (1H, dd, 11.2, 16.1 Hz), 6.71 (1H, d, 16.1 Hz), 6.42 (1H, s), 6.15 (1H, t, 11.2 Hz), 5.91 (1H, m), 5.58 (1H, dd, 3.7, 11.2 Hz), 5.30 (1H, m), 5.27 (1H, dd, 1.7, 17.3 Hz), 5.16 (1H, br d, 10.5 Hz), 4.50 (2H, m), 4.18–4.06 (2H, m), 3.91 (1H, d, 16.1 Hz), 3.80 (1H, d, 16.1 Hz), 3.35 (1H, m), 3.12–3.07 (2H, m), 3.01 (1H, m), 2.41 (1H, m), 1.76–1.30 (9H, m), 1.52 (3H, d, 6.6 Hz) FAB-MS m/z: 563 [M+H]$^+$

EXAMPLE 28

Compound 28

6-Aminooxyhexanoic acid hydrochloride (270 mg) was added to a pyridine solution (2 ml) of radicicol (430 mg), and the mixture was stirred at room temperature for 12 hours and then at 60° C. for 1 hour. The solvent was evaporated under reduced pressure and then the resulting residue was purified by silica gel column chromatography (2% methanol/chloroform) to obtain 213 mg of Compound 28.

$^1$H-NMR ($CD_3OD$) δ (ppm): 7.23 (1H, dd, 11.3, 16.2 Hz), 6.71 (1H, d, 16.2 Hz), 6.42 (1H, s), 6.15 (1H, dd, 10.8, 11.3 Hz), 5.58 (1H, dd, 3.6, 10.8 Hz), 5.30 (1H, m), 4.16–4.08 (2H, m), 3.91 (1H, d, 16.1 Hz), 3.80 (1H, d, 16.1 Hz), 3.33 (1H, m), 3.02 (1H, m), 2.42 (1H, m), 2.30 (2H, m), 1.77–1.45 (7H, m), 1.52 (3H, d, 6.5 Hz) FAB-MS m/z: 494 [M+H]$^+$

EXAMPLE 29

Compound 29

Aminooxyacetic acid hemihydrochloride (1.0 g) was added to a pyridine solution (5 ml) of radicicol (1.5 g), and the mixture was stirred at room temperature for 20 hours and then at 60° C. for 1.5 hours. The solvent was evaporated under reduced pressure and then the resulting residue was purified by silica gel column chromatography (2% methanol/chloroform) to obtain 692 mg of Compound 29.

$^1$H-NMR ($CD_3OD$) δ (ppm): 7.27 (1H, dd, 11.2, 16.1 Hz), 6.82 (1H, d, 16.1 Hz), 6.42 (1H, s), 6.17 (1H, dd, 10.5, 11.2 Hz), 5.61 (1H, dd, 3.4, 10.5 Hz), 5.31 (1H, m), 4.64 (2H, m), 3.91 (1H, d, 16.4 Hz), 3.82 (1H, d, 16.4 Hz), 3.34 (1H, m), 3.02 (1H, m), 2.42 (1H, m), 1.60 (1H, ddd, 4.2, 9.0, 14.4 Hz), 1.53 (3H, d, 6.6 Hz) FAD-MS m/z: 438 [M+H]$^+$

EXAMPLE 30

Compound 30

N-Hydroxysuccinimide (2.5 g) and 4-dimethylaminopyridine (310 mg) were added in that order to a tetrahydrofuran solution (100 ml) of Compound 29 (5.2 g), the mixture was stirred for several minutes and then a tetrahydrofuran solution (30 ml) of dicyclohexylcarbodiimide (4.5 g) was added dropwise thereto at room temperature. After 2 hours of stirring at room temperature, the thus precipitated urea derivative was removed by filtration, and the resulting filtrate was concentrated under reduced pressure to obtain crude crystals of succinimide ester. The succinimide ester thus obtained was dissolved in 100 ml of dichloromethane and mixed with triethylamine (4.5 ml) and dimethylamine hydrochloride (2.0 g) in that order and then the mixture was stirred at room temperature. After 12 hours of the stirring, the reaction solvent was evaporated under reduced pressure, and the residue thus obtained was dissolved in ethyl acetate (500 ml), washed with 1 N hydrochloric acid aqueous solution and saturated sodium chloride aqueous solution and then dried with anhydrous sodium sulfate. This was purified by silica gel column chromatography (100 g; 2% methanol/chloroform) to obtain 2 g of Compound 30.

$^1$H-NMR ($CD_3OD$) δ (ppm): 7.27 (1H, dd, 11.3, 16.1 Hz), 6.81 (1H, d, 16.1 Hz), 6.42 (1H, s), 6.17 (1H, dd, 10.5, 11.3 Hz), 5.61 (1H, dd, 3.5, 10.5 Hz), 5.30 (1H, m), 3.91 (1H, d, 16.1 Hz), 3.82 (1H, d, 16.1 Hz), 3.34 (1H, m), 3.08 (3H, s), 3.02 (1H, dd, 2.2, 3.7, 8.9 Hz), 2.95 (3H, s), 2.42 (1H, ddd, 3.6, 3.7, 14.5 Hz), 1.60 (1H, ddd, 4.1, 8.9, 14.5 Hz), 1.52 (3H, d, 6.6 Hz) FAB-MS m/z 465 [M+H]$^+$

EXAMPLE 31

Compound 31

Radicicol (364 mg) and O-(3-hydroxypropyl) hydroxylamine hydrochloride (137 mg) were dissolved in 3 ml of pyridine and stirred at room temperature for 64 hours. The reaction solvent was evaporated under reduced pressure and then the resulting residue was purified by silica gel column chromatography (15 g; 1.5% methanol/chloroform) to obtain 186 mg of Compound 31.

$^1$H-NMR ($CD_3OD$) δ (ppm): 7.23 (1H, dd, 11.3, 16.1 Hz), 6.72 (1H, d, 16.1 Hz), 6.42 (1H, s), 6.15 (1H, dd, 10.6, 11.3 Hz), 5.59 (1H, dd, 3.5, 10.6 Hz), 5.30 (1H, m), 4.22 (2H, m), 3.91 (1H, d, 16.1 Hz), 3.80 (1H, d, 16.1 Hz), 3.67 (2H, m), 3.33 (1H, m), 3.01 (1Hr m), 2.41 (1H, m), 1.92 (2H,. m), 1.58 (1H, m), 1.52 (3H, d, 6.5 Hz) FAB-MS m/z 438 [M+H]$^+$

EXAMPLE 32

Compound 32

Triethylamine (0.2 ml) and 4-dimethylaminopyridine (78 mg) were added to a dichloromethane solution (6 ml) of Compound 9 (100 mg), and a tetrahydrofuran solution (2 ml) of palmitoyl chloride (0.2 ml) was added dropwise to the mixture which was cooled in an ice bath. This was stirred at 0° C. for 1 hour and then at room temperature for 2 hours, subsequently evaporating the solvent under reduced pressure. The residue thus obtained was dissolved in diethyl ether, washed with saturated ammonium chloride aqueous solution, saturated sodium bicarbonate aqueous solution and saturated sodium chloride aqueous solution and then purified by silica gel column chromatography (15 g; 20% ethyl acetate/hexane) to obtain 156 mg of Compound 32.

$^1$H-NMR ($CDCl_3$) δ (ppm): 7.09 (1H, dd, 11.3, 16.2 Hz), 6.98 (1H, s), 6.73 (1H, d, 16.2 Hz), 6.09 (1H, dd, 10.7, 11.3 Hz), 5.64 (1H, dd, 3.1, 10.7 Hz), 5.34 (1H, m), 4.02 (1H, d, 16.3 Hz), 3.96 (3Hr s), 3.73 (1H, d, 16.3 Hz), 3.43 (1H, m), 2.97 (1H, m), 2.57 (2H, m), 2.46 (2H, m), 2.41 (1H, m), 1.77–1.59 (4H, m), 1.56 (3H, d, 6.5 Hz), 1.46–1.26 (48H, m), 0.88 (6H, t, 6.8 Hz) FAB-MS m/z 870 [M+H]$^+$

EXAMPLE 33

Compound 33

Two drops of concentrated hydrochloric acid (36%) was added to a dioxane solution (1.5 ml) of Compound 9 (33 mg), and the mixture was allowed to stand at room temperature for 30 minutes. The reaction solution was diluted with ethyl acetate (5 ml), washed twice with water and then dried with anhydrous sodium sulfate. This was purified by silica gel preparative thin layer chromatography (0.5 ml×10 cm×20 cm; chloroform-methanol-acetic acid, 194:5:1) to obtain 12 mg of Compound 33.

$^1$H-NMR ($CD_3OD$) δ (ppm): 6.66 (2H, m), 6.42 (1H, s), 6.10 (1H, m), 5.80 (1H, t, 10.3 Hz), 5.32 (1H, m), 4.97 (1H, dd, 3.4, 10.3 Hz), 4.59 (1H, d, 15.4 Hz), 3.89 (3H, s), 3.84 (1H, m), 3.67 (1H, d, 15.4 Hz), 2.09 (1H, m), 1.94 (1H, m), 1.45 (3H, d, 6.1 Hz) FAB-MS m/z 430 [M+H]$^+$

EXAMPLE 34

Compound 34

Using Compound 9 (22 mg), 8 mg of Compound 34 was obtained according to the procedure of Example 3.

$^1$H-NMR ($CD_3OD$) δ (ppm): 6.63 (2H, m), 6.42 (1H, s), 5.99 (1H, m), 5.93 (1H, t, 10.3 Hz), 5.31 (1H, m), 5.10 (1H, dd, 3.6, 10.3 Hz), 4.65 (1H, d, 15.7 Hz), 3.68 (1H, m), 3.67 (1H, d, 15.7 Hz), 2.03 (1H, m), 1.97 (1H, ddd, 3.6, 9.8, 14.4 Hz), 1.44 (3H, d, 6.0 Hz) FAB-MS m/z 474, 476 [M+H]$^+$

EXAMPLE 35

Compound 35

While cooling in an ice bath, 0.16 ml of oxalyl chloride was added dropwise to a dimethylformamide solution (7 ml) of Compound 9 (362 mg). This was stirred in the ice bath for 30 minutes and then at room temperature for 15 hours. The reaction solution was diluted with 50 ml of ethyl acetate, washed twice with water and then dried with anhydrous sodium sulfate. By carrying out purification with silica gel column chromatography (10 g; 2% methanol/chloroform), 94 mg of Compound 35 was obtained.

$^1$H-NMR ($CD_3OD$) δ (ppm): 8.10 (1H, s), 6.87 (1H, d, 16.0 Hz), 6.75 (1H, dd, 11.1, 16.0 Hz), 6.49 (1H, s), 6.19 (1H, t, 11.1 Hz), 5.58 (1H, t, 11.1 Hz), 5.45 (1H, m), 5.32 (1H, m), 5.27 (1H, dd, 4.5, 11.1 Hz) 3.91 (3H, s), 3.85 (1H, d, 15.9 Hz), 3.75 (1H, d, 15.9 Hz), 2.03 (1H, m), 1.95 (1H, dd, 4.8, 14.4 Hz), 1.51 (3H, d, 6.4 Hz) FAB-MS m/z 458 [M+H]$^+$

EXAMPLE 36

Compound 36

Using Compound 30 (410 mg), 188 mg of Compound 36 was obtained according to the procedure of Example 33.

$^1$H-NMR ($CD_3OD$) δ (ppm): 6.78 (1H, d, 16.0 Hz), 6.70 (1H, dd, 10.8, 16.0 Hz), 6.42 (1H, s), 6.10 (1H, dd, 10.8, 11.4 Hz) 5.82 (1H, t, 11.4 Hz), 5.33 (1H, m), 4.98 (1H, dd, 3.1, 11.4 Hz), 4.87–4.79 (2H, m), 4.61 (1H, d, 15.1 Hz), 3.84 (1H, m), 3.67 (1H, d, 15.1 Hz), 3.07 (3H, s), 2.95 (3H, s), 2.09 (1H, m), 1.93 (1H, m), 1.45 (3H, d, 6.0 Hz) FAB-MS m/z 501 [M+H]$^+$

EXAMPLE 37

Tablets

Compound 4 (50 g), lactose (40 g), corn starch (68 g) and carboxymethyl cellulose potassium (10 g) were mixed, and the mixture was kneaded by adding a 10% hydroxypropyl cellulose solution. The kneaded solution was applied to an extrusion granulating machine to make granules which were then mixed with magnesium stearate to obtain whole grain to be used as granules for tablet making use. This was applied to a tablet making machine in the usual way to obtain tablets containing 50 mg of Compound 4 in one tablet (170 mg).

EXAMPLE 38

Capsules

A mixture consisting of 30 g of Compound 4, 80 g of lactose and 58 g of potato starch was kneaded by adding a 10% hydroxypropyl cellulose solution. The kneaded solution was applied to an extrusion granulating machine to make granules which were then mixed with magnesium stearate and packed in hard capsules using an encapsulating machine to obtain capsules containing 30 mg of Compound 4 in one capsule (170 mg).

EXAMPLE 39

Soft Capsules

Compound 4 (10 g) was dissolved in 100 g of soybean oil, and the solution thus obtained was injected into capsules in the usual way to prepare soft capsules containing 10 mg of Compound 4 in one capsule (110 mg).

REFERENCE EXAMPLE 1

14,16-Dipalmitoylradicicol (Compound a)

A toluene solution (150 ml) of radicicol (5 g), pyridine (3.3 ml) and 4-dimethylaminopyridine (1.2 g) was cooled to 0° C., palmitoyl chloride (12.5 ml) was slowly added dropwise to the solution, and the resulting mixture was stirred at 0° C. for 30 minutes. The reaction solution was diluted with chloroform (400 ml) and washed with dilute hydrochloric acid aqueous solution, saturated sodium bicarbonate aqueous solution and saturated brine. This was dried with anhydrous sodium sulfate and then purified by silica gel column chromatography (4:1 n-hexane/ethyl acetate) to obtain 12 g of Compound a.

$^1$H-NMR ($CDCl_3$) δ (ppm): 7.52 (1H, dd, 10.3, 16.1 Hz), 7.02 (1H, s), 6.15 (1H, t, 10.3 Hz), 6.06 (1H, d, 16.1 Hz), 5.79 (1H, dd, 3.9, 10.3 Hz), 5.40 (1H, m), 4.03 (1H, d, 16.4 Hz), 3.92 (1H, d, 16.4 Hz), 3.52 (1H, m), 3.02 (1H, ddd, 2.2, 2.2, 7.8 Hz), 2.58 (2H, t, 7.6 Hz), 2.49 (2H, ddd, 1.7, 7.3, 7.3 Hz), 2.40 (1H, 3.4, 3.4, 14.7 Hz), 1.78–1.60 (5H, m), 1.54 (3H, d, 6.6 Hz), 1.49–1.23 (48H, m), 0.88 (6H, t, 6.8 Hz). FAB-MS m/z: 841 [M+H]$^+$

INDUSTRIAL APPLICABILITY

The radicicol derivative of the present invention can be used in pharmaceutical preparations which have antitumor, antibacterial or immunosuppression effects.

What is claimed is:

1. A radicicol derivative represented by the following formula (I) or a pharmacologically acceptable salt thereof:

(I)

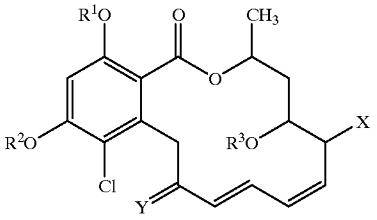

wherein $R^1$ and $R^2$ independently represent hydrogen, alkanoyl, alkenoyl or tert-butyldimethylsilyl; X is a halogen or is combined with $R^3$ to represent a single bond, provided:

(1) when X represents halogen, Y represents an oxygen atom or $R^4$—O—N, wherein $R^4$ represents hydrogen, or substituted or unsubstituted lower alkyl, said lower alkyl substituent is selected from the group consisting of hydroxyl, lower alkoxy, lower alkanoyloxy, azido, amino, mono- or di-lower alkylamino, lower alkanoylamino, lower alkoxycarbonylamino, lower alkenyloxycarbonylamino, carboxyl, lower alkoxycarbonyl, lower alkylcarbamoyl and cyclic imido; and $R^3$ represents hydrogen, alkanoyl, alkenoyl or —SO—Z, wherein Z represents the following formula (A):

(A)

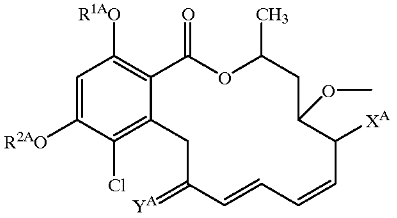

wherein $X^A$, $R^{1A}$ and $R^{2A}$ are defined as X, $R^1$ and $R^2$, respectively; and $Y^A$ represents an oxygen atom or $R^{4A}$—O—N, wherein $R^{4A}$ is defined as $R^4$; and (2) when X and $R^3$ are combined with each other to represent a single bond, Y represents $R^{4B}$—O—N, wherein $R^{4B}$ is defined as $R^4$.

2. The compound according to claim 1, wherein X is halogen.

3. The compound according to claim 1, wherein Y is $R^4$—O—N.

4. A method for treating diseases caused by disordered increases in tyrosine kinase comprising administering a therapeutic composition comprising at least one compound according to any one of claims 1 to 3, and a pharmaceutically acceptable carrier.

* * * * *

UNITED STATES PATENT AND TRADEMARK OFFICE
CERTIFICATE OF CORRECTION

PATENT NO. : 5,977,165

DATED : November 2, 1999

INVENTOR(S) : TSUTSOMU AGATSUMA, et al.

It is certified that error appears in the above-identified patent and that said Letters Patent is hereby corrected as shown below:

ON TITLE PAGE

[56] Under Other Publications, after "Cancer Research": "(Dec. 1992" should read --(Dec. 1992)--.

COLUMN 3

Line 24, "with" should read --will--.

COLUMN 9

Table 1(2), In compound 21, "$CH_3(CH_2)_{14}CO$ Cl" should read --$CH_3(CH_2)_{14}CO$ Br--; and Line 57, "e" should read --single--.

COLUMN 12

Line 33, "Tumors" should read --Tumor:--.

UNITED STATES PATENT AND TRADEMARK OFFICE

CERTIFICATE OF CORRECTION

PATENT NO. : 5,977,165

DATED : November 2, 1999

INVENTOR(S) : TSUTSOMU AGATSUMA, et al.

It is certified that error appears in the above-identified patent and that said Letters Patent is hereby corrected as shown below:

COLUMN 24

Line 2, "FAD-MS" should read --FAB-MS--.

Signed and Sealed this

Fifth Day of December, 2000

Attest:

Q. TODD DICKINSON

Attesting Officer

Director of Patents and Trademarks